US012133859B2

(12) United States Patent
Bhatt et al.

(10) Patent No.: US 12,133,859 B2
(45) Date of Patent: *Nov. 5, 2024

(54) TOPICAL COMPOSITIONS

(71) Applicant: BAUSCH HEALTH IRELAND LIMITED, Dublin (IE)

(72) Inventors: Varsha Bhatt, San Francisco, CA (US); Radhakrishnan Pillai, Santa Rosa, CA (US); Arturo Angel, Santa Rosa, CA (US)

(73) Assignee: BAUSCH HEALTH IRELAND LIMITED, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 18/639,619

(22) Filed: Apr. 18, 2024

(65) Prior Publication Data

US 2024/0325423 A1    Oct. 3, 2024

Related U.S. Application Data

(63) Continuation of application No. 17/835,935, filed on Jun. 8, 2022, which is a continuation of application No. 16/945,067, filed on Jul. 31, 2020, now Pat. No. 11,389,467.

(60) Provisional application No. 62/881,836, filed on Aug. 1, 2019.

(51) Int. Cl.
| *A61K 31/7056* | (2006.01) |
| *A61K 8/22* | (2006.01) |
| *A61K 8/34* | (2006.01) |
| *A61K 8/49* | (2006.01) |
| *A61K 8/73* | (2006.01) |
| *A61K 9/00* | (2006.01) |
| *A61K 9/06* | (2006.01) |
| *A61K 31/192* | (2006.01) |
| *A61K 31/327* | (2006.01) |
| *A61K 47/02* | (2006.01) |
| *A61K 47/10* | (2017.01) |
| *A61K 47/32* | (2006.01) |
| *A61P 17/10* | (2006.01) |
| *A61Q 19/00* | (2006.01) |

(52) U.S. Cl.
CPC ............ *A61K 31/7056* (2013.01); *A61K 8/22* (2013.01); *A61K 8/345* (2013.01); *A61K 8/4913* (2013.01); *A61K 8/731* (2013.01); *A61K 9/0014* (2013.01); *A61K 9/06* (2013.01); *A61K 31/192* (2013.01); *A61K 31/327* (2013.01); *A61K 47/02* (2013.01); *A61K 47/10* (2013.01); *A61K 47/32* (2013.01); *A61P 17/10* (2018.01); *A61Q 19/005* (2013.01)

(58) Field of Classification Search
CPC ...... A61K 31/7056; A61K 8/22; A61K 8/345; A61K 8/4913; A61K 8/731; A61K 9/0014; A61K 9/06; A61K 31/192; A61K 31/327; A61K 47/02; A61K 47/10; A61K 47/32; A61P 17/10; A61Q 19/005

USPC ............................................................ 514/62
See application file for complete search history.

(56) References Cited

U.S. PATENT DOCUMENTS

| 8,288,434 | B2 | 10/2012 | Chang et al. |
| 8,445,543 | B2 | 5/2013 | Vernet et al. |
| 8,703,820 | B2 | 4/2014 | Graeber et al. |
| 8,729,127 | B2 | 5/2014 | Graeber et al. |
| 8,785,420 | B2 | 7/2014 | Vernet et al. |
| 8,809,305 | B2 | 8/2014 | Graeber et al. |
| 8,936,800 | B2 | 1/2015 | Orsoni et al. |
| 9,381,179 | B2 | 7/2016 | Graeber et al. |
| 9,387,187 | B2 | 7/2016 | Graeber et al. |
| 9,561,208 | B2 | 2/2017 | Chang et al. |
| 9,814,690 | B2 | 11/2017 | Orsoni et al. |
| 10,220,049 | B2 | 3/2019 | Chang et al. |
| 10,624,918 | B2 | 4/2020 | Chang et al. |
| 11,389,467 | B2 * | 7/2022 | Bhatt ............... A61P 17/10 |
| 2007/0003585 | A1 * | 1/2007 | Clark ............... A61P 17/10 514/568 |
| 2009/0318371 | A1 | 12/2009 | Ahumada Ayala |
| 2010/0210571 | A1 | 8/2010 | Popp |
| 2016/0120797 | A1 | 5/2016 | Rayudu |
| 2018/0235924 | A1 | 8/2018 | Toledano et al. |

FOREIGN PATENT DOCUMENTS

| AU | 2014216045 A1 | 3/2016 |
| CN | 102056481 A | 6/2009 |
| JP | 2009-500336 A | 1/2009 |
| JP | 2011-522820 A | 8/2011 |
| WO | 2007002831 A2 | 1/2007 |
| WO | 2009148584 A1 | 12/2009 |

OTHER PUBLICATIONS

Kircik, L., "Synergy and Its Clinical Relevance in Topical Acne Therapy," J Clin Aesthet Dermatol., vol. 4, No. 11, p. 30-33, (2011).
Leyden, J., "Antibiotic-Resistant Propionibacterium acnes Suppressed by a Benzoyl Peroxide Cleanser 6%," Cutis., vol. 82, p. 417-421, (2008).
Stein Gold et al., "Efficacy and Safety of a Fixed-Dose Clindamycin 1.2%, Benzoyl Peroxide 3.1 %, and Adapalene 0.15% Gel for Moderate-to-Severe Acne: Randomized Phase 2 and Phase 3 Studies of the First Triple-Combination Drug," Poster Presentation from DERM 2022, presented Jul. 29-31, 2022 in Las Vegas, Nevada.

(Continued)

*Primary Examiner* — Yih-Horng Shiao
(74) *Attorney, Agent, or Firm* — Morgan, Lewis & Bockius LLP

(57) ABSTRACT

The disclosure provides a topical gel formulation comprising 1-1.5 wt. % clindamycin phosphate, 2.5-3.5 wt. % benzoyl peroxide, and 0.1-0.2 wt. % adapalene, in combination with a gelling agent, a polyhydric alcohol, and water, useful in treating inflammatory skin conditions, including acne, together with methods of making and using the same.

20 Claims, No Drawings

(56) References Cited

OTHER PUBLICATIONS

Zaenglein et al., "Guidelines of Care for the Management of Acne Vulgaris," J Am Acad Dermatol., vol. 74, p. 945-973, (2016).
Bowman et al., "Comparison of Clindamycin/Benzoyl Peroxide, Tretinoin Plus 4. Clindamycin, and the Combination of Clindamycin/ Benzoyl Peroxide and Tretinoin Plus Clindamycin in the Treatment of Acne Vulgaris: A Randomized, Blinded Study," J Drugs Dermatol., vol. 4, No. 5, pp. 611-618 (2005); Abstract Only.
"Safety and Efficacy Study of Clindamycin/Benzoyl Peroxide/ Tazarotene Cream in Subjects with Acne," Clinical Trial Identifier: NCT00713609, 10 pages, Webpage <https :/ /clinicaltrials.gov /ct2/show/study/NCT00713609?term=NCT00713609&draw= 2&rank= 1> published on Jul. 11, 2008 and retrieved on May 4, 2022.
Stein Gold et al., "Efficacy and Safety of a Fixed-Dose Clindamycin Phosphate 6. 1.2%, Benzoyl Peroxide 3.1 %, and Adapalene 0.15% Gel for Moderate-to-Severe Acne: a Randomized Phase II Study of the First Triple-Combination Drug," Am. J. Clin. Dermatol., vol. 23, No. 1, pp. 93-104, (2021).
Zaenglein, A. L., "Topical retinoids in the treatment of acne vulgaris," Semin. Cutan. Med. Surg., vol. 27, No. 3, pp. 177-182, (2008).
Office Action issued in corresponding Canadian Application No. 3,149,296, dated Dec. 13, 2023, 4 pages.
Office Action issued in corresponding European Application No. 20750261.8, dated Nov. 14, 2023, 7 pages.
Office Action issued in corresponding Russian Application No. 2022104310, dated Dec. 15, 2023, 12 pages.
Benzaclin Gel—Uses, Side Effects, and More, WebMD. Found on the Internet Oct. 8, 2017. The link to the Internet source: https:// web.archive.org/web/20170810075357/https://www.webmd.com/ drugs/2/drug-20405/benzaclin-topical/details.
Office Action issued in corresponding Ukrainian Application No. a202200895, dated Feb. 19, 2024, 9 pages, with English translation.
Office Action issued in corresponding Chinese Patent Application No. 202080052185.4, dated Feb. 8, 2024, 23 pages, with English translation.
Office Action issued in corresponding Japanese Patent Application No. 2022-506666 dated Jun. 11, 2024, 6 pages.
Office Action issued in corresponding Saudi Arabian Patent Application No. 522431568 dated Aug. 2, 2024, 7 pages, with English summary.

* cited by examiner

TOPICAL COMPOSITIONS

CROSS REFERENCE TO RELATED APPLICATIONS

This application is a continuation of U.S. patent application Ser. No. 17/835,935, filed Jun. 8, 2022, which is a continuation of U.S. patent application Ser. No. 16/945,067, filed Jul. 31, 2020, now U.S. Pat. No. 11,389,467, which claims priority to U.S. Provisional Application No. 62/881,836, filed Aug. 1, 2019, the contents of each are incorporated herein by reference in their entireties.

FIELD

This disclosure relates to topical compositions for the treatment of dermatological conditions, including acne. In particular, the disclosure provides topical compositions comprising three different active ingredients, and methods for making and using the same.

BACKGROUND

Acne is a very common disorder of sebaceous follicles that is most prevalent among teenagers, usually triggered by the increase in androgen production occurring at puberty. Although acne generally resolves by the age of 25, approximately 3% to 8% of adults 25 to 44 years of age present with acne. The pathogenesis is complex and appears to involve 4 primary features: stimulation of sebum gland activity, bacterial proliferation (especially *Cutibacterium acnes*, previously known as *Propionibacterium acnes*), abnormal follicular hyperkeratinization and resultant obstruction of the sebaceous follicles, and the release of inflammatory mediators. These changes in acne patients result in the formation of clinical inflammatory lesions including superficial pustules such as comedones (popularly known as "blackheads" or "whiteheads") and more deeply located papules, nodules, and cysts. The areas most affected by the disease include the pilosebaceous follicles of the head and upper trunk, where the sebaceous glands are particularly active.

Elevated production of oily sebum and keratin, leading to acne, is influenced by individual genetics, a wide variety of medications (e.g., corticosteroids, androgens, or lithium, azathioprine, haloperidol, Vitamin D, Vitamin B12, halogens such as iodides or bromides, phenytoin, or phenobarbital), and possibly other factors, such as diet and stress. Elevated sebum and keratin production correlates with elevated levels of various hormones, including androgens (e.g., testosterone, dihydrotestosterone (DHT), and dehydroepiandrosterone (DHEA)), growth hormone (GH), and insulin-like growth factor 1 (IGF-1). Infection of the follicle by anaerobic bacteria (e.g. *C. acnes*) and/or by the parasitic mite *Demodex folliculorum* may exacerbate the condition, although whether infection is involved in initiating the condition is unclear.

Current treatment options for acne include (i) retinoids and retinoid-like drugs, such as tretinoin (Avita, Retin-A, others), adapalene (Differin) and tazarotene (Tazorac, Avage); antibiotics, including clindamycin with benzoyl peroxide (Benzaclin, Duac, Acanya) and erythromycin with benzoyl peroxide (Benzamycin); salicylic acid and azelaic acid; and dapsone (Aczone).

Benzoyl peroxide is commonly found in over-the-counter products to treat acne, and prescription products in combination with antibiotics. While the exact mechanism of action is unclear, it is bacteriocidal, it breaks down keratin, thereby helping to unclog the pores, and it may inhibit sebum production. Benzoyl peroxide formulations, however, may cause local irritation, both because benzoyl peroxide is a powerful oxidant, and because, being nearly insoluble in water, it is often formulated with harsh organic solvents. It is also incompatible with many other compounds, due to its high chemical reactivity.

Clindamycin for topical administration may be administered in the form of clindamycin phosphate, a phosphate ester prodrug of clindamycin. In addition to its antibiotic effects, clindamycin has anti-inflammatory effects. One disadvantage of clindamycin (and other antibiotics) is the risk of developing antibiotic-resistant bacterial populations on the skin.

Adapalene is a retinoid compound that is an agonist for specific retinoic acid nuclear receptors. It modulates cellular differentiation, keratinization, and inflammatory processes, and topical formulations have been approved for treating acne. Although the exact mode of action of adapalene is unknown, it may normalize the differentiation of follicular epithelial cells, resulting in decreased microcomedone formation.

Combination products have been tried, but the results have been quite unpredictable. For example, Bowman, S. et al., "Comparison of clindamycin benzoyl peroxide, tretinoin plus clindamycin, and the combination of clindamycin benzoyl peroxide and tretinoin plus clindamycin in the treatment of acne vulgaris: a randomized, blinded study." J Drugs Dermatol. 2005 September-October; 4(5):611-8, reported that while regimens that included clindamycin/benzoyl peroxide were more effective than a retinoid (tretinoin) plus clindamycin in treating acne, there was no clinical advantage to adding a retinoid plus clindamycin to once-daily clindamycin/benzoyl peroxide treatment. Similar results were seen in a large trial studying a combination treatment with a benzoyl peroxide 5%/clindamycin 1% gel and a different retinoid, tazarotene. Clinical Trial NCT00713609, results posted March 2017, available on clinicaltrials.gov. After 12 weeks, there were no statistically significant differences between active combination treatment groups in lesion count reduction. The triple combination was no better and in fact had numerically lower reduction in lesion counts, compared to dual therapies. Often, such combination therapies are administered with one or two drugs in the morning and the other drug or drugs in the evening, which is less convenient for the patients than a single daily treatment, but may reduce unpredictable detrimental interactions among the drugs.

While various treatments for acne are known, there is still a need for more effective treatments. The lack of understanding and consensus regarding both the complex pathogenesis of the condition and the precise mechanism(s) of action of common treatment agents make it difficult to design effective treatments and demonstrating efficacy and lack of side effects requires expensive clinical trials. Simply increasing the concentration of existing active agents may result in irritation and other side effects. Combinations of active agents may be constrained due to unpredictable chemical interactions between the agents, unpredictable effects of one agent on the delivery of another agent, unpredictable efficacy, and potential for unpredictable side effects. There is a need for improved formulations to treat acne, providing better efficacy without unacceptable side effects.

SUMMARY

We have surprisingly found that a topical gel containing a fixed combination of benzoyl peroxide, clindamycin phosphate, and adapalene, administered on a daily basis, provides significantly enhanced efficacy compared to gels containing combinations of any two of these agents.

Each of these agents has some degree of anti-inflammatory activity; both the benzoyl peroxide and the clindamycin phosphate decrease *C. acnes* proliferation); benzoyl peroxide is also keratolytic; and adapalene additionally regulates keratinization (Zaenglein 2008). A fixed-dose combination treatment is optimal to enhance patient adherence due to simplified application regimens (e.g., once daily versus sequential morning/evening administration of each active agent) and also to preclude substance incompatibilities due to application errors (e.g., oxidation by using incompatible single agents). Whether such a fixed dose formulation could be designed to be stable, safe and effective, however, required empirical testing.

The disclosure provides, in one embodiment, a topical gel formulation comprising 1-1.5 wt. % (e.g., about 1.2 wt. %) clindamycin phosphate, 2.5-3.5 wt. % (e.g., about 3.1 wt. %) benzoyl peroxide, and 0.1-0.2 wt. % (e.g., about 0.15 wt. %) adapalene, in combination with a gelling agent (e.g., a carbomer homopolymer), a polyhydric alcohol (e.g., propylene glycol), and water. In another embodiment, the disclosure provides a method of treating acne vulgaris comprising administering to the affected area, e.g., once daily, e.g., for at least 12 weeks, a topical gel formulation comprising 1-1.5 wt. % (e.g., about 1.2 wt. %) clindamycin phosphate, 2.5-3.5 wt. % (e.g., about 3.1 wt. %) benzoyl peroxide, and 0.1-0.2 wt. % (e.g., about 0.15 wt. %) adapalene, in combination with a gelling agent (e.g., a carbomer homopolymer), a polyhydric alcohol (e.g., propylene glycol), and water.

In another embodiment, the disclosure provides a method of making a topical gel formulation, e.g., as described above, comprising mixing 1-1.5 wt. % (e.g., about 1.2 wt. %) clindamycin phosphate, 2.5-3.5 wt. % (e.g., about 3.1 wt. %) benzoyl peroxide, 0.1-0.2% (e.g., about 0.15 wt. %) adapalene, gelling agent (e.g., a carbomer homopolymer), a polyhydric alcohol (e.g., propylene glycol), and water, to form a dispersion, and then adjusting the pH of the combination to pH 5-6.

Further areas of applicability of the present disclosure will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

In a first embodiment, the disclosure provides a topical gel formulation (Formulation 1) comprising 1-1.5 wt. % clindamycin phosphate, 2.5-3.5 wt. % benzoyl peroxide, and 0.1-0.2 wt. % adapalene, a gelling agent, a polyhydric alcohol, and water; for example, 1.1. Formulation 1 wherein the concentration of clindamycin phosphate is about 1.2 wt. %.
1.2. Formulation 1 or 1.1 wherein the concentration of benzoyl peroxide is about 3.1 wt. %.
1.3. Any foregoing formulation wherein the concentration of adapalene is about 0.15 wt. %.
1.4. Any foregoing formulation wherein the gelling agent is selected from hydroxypropylcellulose, hydroxyethylcellulose, carboxyvinyl polymers (optionally crosslinked with allyl ethers of polyalcohols, e.g., carbomers), carboxyvinyl copolymers, polyacrylates, acrylate copolymers, acrylamide/sodium acryloyldimethyltaurate copolymers, polyvinyl alcohols, polyethylene oxides, propylene glycol alginates, methylcellulose, hydroxypropylmethylcellulose, xanthan gum, carrageenan gum, and combinations thereof.
1.5. Any foregoing formulation wherein the gelling agent is selected from carboxyvinyl polymers (optionally crosslinked with allyl ethers of polyalcohols, e.g., carbomers), carboxyvinyl copolymers, polyacrylates, acrylate copolymers, acrylamide/sodium acryloyldimethyltaurate copolymers, propylene glycol alginates, hydroxypropylmethylcellulose, and xanthan gum.
1.6. Any foregoing formulation wherein the gelling agent comprises acrylamide/sodium acryloyldimethyltaurate copolymer.
1.7. Any foregoing formulation wherein the gelling agent comprises acrylamide sodium acryloyldimethyltaurate/isohexadecane/polysorbate 80 gelling agent.
1.8. Any foregoing formulation wherein the gelling agent comprises a carbomer homopolymer, crosslinked with allyl ethers of polyalcohols (e.g., allyl sucrose or allyl pentaerythritol).
1.9. Any foregoing formulation wherein the gelling agent is a polymer of acrylic acid cross-linked with allyl ethers of polyalcohols; e.g., containing from 56% to 68% of carboxylic acid (—COOH) groups; e.g., having a viscosity of 40,000-60,000 cPs (measured at 0.5 wt % at pH 7.5).
1.10. Any foregoing formulation wherein the gelling agent is a carbomer homopolymer Type C, e.g., as defined by the United States Pharmacopeia/National Formulary (USP/NF) monograph, e.g., Carbopol 980.
1.11. Any foregoing formulation wherein the amount of gelling agent is 1.5-2 wt. %.
1.12. Any foregoing formulation wherein the amount of gelling agent is about 1.75 wt. %.
1.13. Any foregoing formulation wherein the amount of gelling agent is carbomer homopolymer Type C, in an amount of about 1.75 wt. %.
1.14. Any foregoing formulation wherein the pH of the formulation is pH 5-6.
1.15. Any foregoing formulation wherein the gelling agent is a crosslinked polymer comprising carboxy moieties and wherein the formulation further comprises base selected from potassium hydroxide, sodium hydroxide and combinations thereof in an amount sufficient to deprotonate the carboxy moieties sufficiently to cause the gelling agent to thicken.
1.16. Any foregoing formulation comprising a base selected from potassium hydroxide, sodium hydroxide and combinations thereof in an amount to provide a pH of 5-6.
1.17. Any foregoing formulation comprising a potassium hydroxide in an amount to provide a pH of 5-6.
1.18. Any foregoing formulation wherein a fraction of the benzoyl peroxide is undissolved and wherein the undissolved fraction of the benzoyl peroxide is homogeneously dispersed in the formulation.
1.19. Any foregoing formulation wherein a fraction of the benzoyl peroxide is undissolved and wherein the undissolved fraction of the benzoyl peroxide has a mean particle between 1 and 50 microns, e.g., between 2.5 and 30 microns.

1.20. Any foregoing formulation wherein the benzoyl peroxide is not encapsulated or entrained in a microsponge.
1.21. Any foregoing formulation wherein the benzoyl peroxide is free and unrestricted by any complex or polymer.
1.22. Any foregoing formulation wherein a fraction of the adapalene is undissolved and wherein the undissolved fraction of the adapalene is homogeneously dispersed in the formulation.
1.23. Any foregoing formulation wherein a fraction of the adapalene is undissolved and homogeneously dispersed in the formulation and a fraction of the benzoyl peroxide is also undissolved and homogeneously dispersed in the formulation.
1.24. Any foregoing formulation wherein the adapalene and the benzoyl peroxide do not undergo any substantial chemical reaction with one another.
1.25. Any foregoing formulation wherein the polyhydric alcohol is selected from propylene glycol, ethoxydiglycol, polyethylene glycol (e.g., PEG 400), glycerol, and combinations thereof.
1.26. Any foregoing formulation wherein the polyhydric alcohol is selected from 1,2-propylene glycol and 1,3-proylene glycol.
1.27. Any foregoing formulation wherein the polyhydric alcohol is 1,2-propylene glycol.
1.28. Any foregoing formulation wherein the amount by weight of polyhydric alcohol in the formulation is between one and four times (e.g. one to two times) the amount of benzoyl peroxide.
1.29. Any foregoing formulation wherein the ratio by weight of water to polyhydric alcohol in the formulation is 10:1 to 20:1.
1.30. Any foregoing formulation wherein the amount of polyhydric alcohol is 3-7 wt. %.
1.31. Any foregoing formulation wherein the amount of polyhydric alcohol is about 5 wt. %.
1.32. Any foregoing formulation wherein the polyhydric alcohol is propylene glycol in an amount of about 5 wt. %.
1.33. Any foregoing formulation wherein the amount of water is 80% to 90% by weight, e.g. 85% to 90% by weight.
1.34. Any foregoing formulation wherein the formulation comprises about 1.2 wt. % clindamycin phosphate, about 3.1 wt. % benzoyl peroxide, and about 0.15 wt. % adapalene.
1.35. Any foregoing formulation wherein the formulation comprises about 1.2 wt. % clindamycin phosphate, about 3.1 wt. % benzoyl
peroxide, about 0.15 wt. %
adapalene, about 5 wt. %
propylene glycol,
about 1.75 wt. % carbomer homopolymer Type C,
potassium hydroxide in an amount to provide a pH of 5-6, and
water.
1.36. A formulation comprising about 1.2 wt. % clindamycin phosphate, about 3.1 wt. % benzoyl peroxide, and about 0.15 wt. % adapalene, wherein the formulation is clinically bioequivalent to the preceding formulation, e.g., demonstrated by one or more of (a) a clinical endpoint bioequivalence study, (b) in vitro permeation testing (IVPT), and/or (c) in vitro release testing (IVRT).
1.37. Any foregoing formulation, wherein the formulation is free of ionic surfactants.
1.38. Any foregoing formulation, wherein the formulation is free of organic solvents other than the polyhydric alcohol.
1.39. Any foregoing formulation wherein the formulation contains less than 2% of ethanol or isopropanol, e.g. is free of ethanol and isopropanol.
1.40. Any foregoing formulation wherein the formulation is substantially free of monohydric alcohols.
1.41. Any foregoing formulation wherein the formulation is aqueous.
1.42. Any foregoing formulation wherein the formulation is monophasic.
1.43. Any foregoing formulation wherein the formulation is not an emulsion.
1.44. Any foregoing formulation wherein the formulation does not contain mineral oil.
1.45. Any foregoing formulation, wherein the formulation is free of polymers other than the gelling agent.
1.46. Any foregoing formulation, wherein the formulation is free of polymers other than carbomer homopolymer.
1.47. Any foregoing formulation, wherein the formulation is free of preservatives or antimicrobial agents, other than the benzoyl peroxide and the adapalene.
1.48. Any foregoing formulation, wherein the only active ingredients are clindamycin phosphate, benzoyl peroxide, and adapalene.
1.49. Any foregoing formulation further comprising one or more additional inactive ingredients selected from humectants, emollients, pH stabilizing agents, preservatives, chelating agents, and anti-oxidants.
1.50. Any foregoing formulation further comprising an effective amount of a preservative, e.g., selected from parahydroxybenzoate preservatives (parabens), for example, selected from methylparaben, propylparaben, and combinations thereof.
1.51. Any foregoing formulation which is prepared by mixing 1-1.5 wt. % clindamycin phosphate, 2.5-3.5 wt. % benzoyl peroxide, 0.1-0.2 wt. % adapalene, a gelling agent, a polyhydric alcohol, and water, to form a homogeneous dispersion, and then adding a base selected from potassium hydroxide, sodium hydroxide and combinations thereof in an amount to provide a pH of 5-6.
1.52. Any foregoing formulation wherein the clindamycin phosphate, benzoyl peroxide, and adapalene are present in concentrations effective to treat acne when the formulation is administered once daily to the affected area over a period of at least four, six or eight weeks, e.g., at least 12 weeks.
1.53. Any foregoing formulation, wherein the formulation has fewer side effects than a formulation comprising 2.5-3.5 wt. % benzoyl peroxide and 0.1-0.2 wt. % adapalene.

1.54. Any foregoing formulation, wherein the formulation does not have significantly more side effects than a formulation comprising 2.5-3.5 wt. % benzoyl peroxide and 0.1-0.2 wt. % adapalene.
1.55. Any foregoing formulation, wherein the formulation is more effective in treating acne than a formulation comprising active ingredients selected from (i) 1-1.5 wt. % clindamycin phosphate and 2.5-3.5 wt. % benzoyl peroxide, (ii) 2.5-3.5 wt. % benzoyl peroxide and 0.1-0.2 wt. % adapalene, and (iii) 1-1.5 wt. % clindamycin phosphate and 0.1-0.2 wt. % adapalene.
1.56. Any foregoing formulation wherein the formulation is stable at room temperature for at least six weeks, e.g., at least 10 weeks.
1.57. Any foregoing formulation wherein the formulation is stable when refrigerated, e.g. at 2° C. to 8° C. (36° F. to 46° F.), prior to dispensing to patient, then stable at room temperature, e.g. at or below 25° C. (77° F.), for at least six weeks, e.g., at least 10 weeks.
1.58. Any foregoing formulation for use in treating acne, e.g., by daily topical application to the affected area, e.g., in accordance with any of Method 1, et seq.
1.59. Any foregoing formulation, which is obtained or obtainable by the process of any of Methods 2, et seq.

In another embodiment, the disclosure provides a drug product, which is container containing any of Formulations 1-1.59, e.g., a pump container or a deformable tube containing any of Formulations 1-1.59, e.g., a container comprising a pump and containing any of Formulations 1-1.59, wherein the pump is calibrated to release a specific amount (e.g., 0.5-1 cubic centimeter, e.g., a pea-sized portion) of the formulation each time the pump is pressed.

In another embodiment, the disclosure provides a method (Method 1) of treating acne vulgaris in a patient in need thereof, comprising administering to the affected area on at least a daily basis, a topical gel formulation comprising 1-1.5 wt. % (e.g., about 1.2 wt. %) clindamycin phosphate, 2.5-3.5 wt. % (e.g., about 3.1 wt. %) benzoyl peroxide, and 0.1-0.2 wt. % (e.g., about 0.15 wt. %) adapalene, a gelling agent (e.g., a carbomer homopolymer), a polyhydric alcohol (e.g., propylene glycol), and water. For example, the disclosure provides:

1.1. Method 1, wherein administration is once daily.
1.2. Method 1 or 1.1, wherein the affected area is the face, neck, back, and/or chest.
1.3. Any foregoing method wherein the affected area is the face.
1.4. Any foregoing method wherein the administration is to the entire affected area, e.g., to the entire face.
1.5. Any foregoing method wherein a thin layer of the topical gel formulation is once daily in the evening, at least 30 minutes prior to bed time, at about the same time every day, to the entire face for twelve weeks.
1.6. Any foregoing method wherein the amount of topical gel formulation is used per application is approximately 0.5-1 cubic centimeters (a pea-sized amount).
1.7. Any foregoing method, wherein the patient is at least 9 years of age.
1.8. Any foregoing method, wherein the patient has a clinical diagnosis of moderate to severe acne.
1.9. Any foregoing method wherein the patient has acne with a score of 3 or 4 based on the following Evaluator's Global Severity Score (EGSS):

| Score | Grade | Description |
|---|---|---|
| 0 | Clear | Normal, clear skin with no evidence of acne vulgaris |
| 1 | Almost clear | Rare non-inflammatory lesions present, with rare non-inflamed papules (papules must be resolving and may be hyperpigmented, though not pink-red) |
| 2 | Mild | Some non-inflammatory lesions are present, with few inflammatory lesions (papules/pustules only; no nodulocystic lesions) |
| 3 | Moderate | Non-inflammatory lesions predominate, with multiple inflammatory lesions evident: several to many comedones and papules/pustules, and there may or may not be one nodulocystic lesion |
| 4 | Severe | Inflammatory lesions are more apparent, many comedones and papules/pustules, there may or may not be up to two nodulocystic lesions |

1.10. Any foregoing method, wherein the treatment continues for at least 4 weeks, e.g., at least 8 weeks, e.g., at least 12 weeks.
1.11. Any foregoing method wherein the treatment continues for at least 12 weeks.
1.12. Any foregoing method wherein the treatment is for a time sufficient to ameliorate the symptoms of the inflammatory skin condition.
1.13. Any foregoing method wherein the inflammatory skin condition is acne vulgaris and the treatment results in an improved score on the Evaluator's Global Severity Score (EGSS).
1.14. Any foregoing method, wherein the administration is once daily in the evening.
1.15. Any foregoing method wherein the treatment has fewer side effects than treatment with a formulation comprising 2.5-3.5 wt. % benzoyl peroxide and 0.1-0.2 wt. % adapalene, e.g., lower incidence of pain and/or dryness at the application site.
1.16. Any foregoing method, wherein the treatment is more effective in treating acne than treatment with a formulation comprising active ingredients selected from (i) 1-1.5 wt. % clindamycin phosphate and 2.5-3.5 wt. % benzoyl peroxide, (ii) 2.5-3.5 wt. % benzoyl peroxide and 0.1-0.2 wt. % adapalene, and (iii) 1-1.5 wt. % clindamycin phosphate and 0.1-0.2 wt. % adapalene.
1.17. Any foregoing method wherein the patient has 20 or more, e.g., 20 to 40, inflammatory lesions on the face, and/or 25 or more, e.g., 25-100, noninflammatory lesions on the face at the start of treatment.
1.18. Any foregoing method wherein the patient has been diagnosed with moderate to severe acne.
1.19. Any foregoing method wherein the patient has an EGSS of 3 (moderate) or 4 (severe) at the start of treatment.
1.20. Any foregoing method wherein the patient is age 9 and up.
1.21. Any foregoing method wherein the patient is age 12 and up
1.22. Any foregoing method wherein at the start of treatment the patient has a facial acne inflammatory lesion (papules, pustules, and nodules) count of no less than 30, but no more than 100.
1.23. Any foregoing method wherein at the start of treatment the patient has a facial acne non-inflammatory lesion (open and closed comedones) count of no less than 35, but no more than 150.
1.24. Any foregoing method wherein the patient is female, is not pregnant, and is using birth control during the entire treatment period.
1.25. Any foregoing method, wherein the topical gel formulation is a formulation selected from any one of Formulations 1-1.59.
1.26. Any foregoing method, wherein the topical gel formulation comprises about 1.2 wt. % clindamycin phosphate, about 3.1 wt. % benzoyl peroxide, and about 0.15 wt. % adapalene.
1.27. Any foregoing method, wherein the topical gel formulation
comprises about 1.2 wt. % clindamycin phosphate,
about 3.1 wt. % benzoyl
peroxide, about 0.15 wt. %
adapalene, about 5 wt. %
propylene glycol,
about 1.75 wt. % carbomer homopolymer Type C,
potassium hydroxide in an amount to provide a pH of 5-6, and
water.
1.28. Any foregoing method, wherein the topical gel formulation is a formulation comprising about 1.2 wt. % clindamycin phosphate, about 3.1 wt. % benzoyl peroxide, and about 0.15 wt. % adapalene, wherein the formulation is clinically bioequivalent to the preceding formulation, e.g., demonstrated by one or more of (a) a clinical endpoint bioequivalence study, (b) in vitro permeation testing (IVPT), and/or (c) in vitro release testing (IVRT).

In another embodiment, the disclosure provides the use of clindamycin phosphate, benzoyl peroxide, and adapalene, in the manufacture of a medicament (e.g., a formulation according to any one of Formulation 1-1.59) for treatment of an inflammatory condition of the skin (e.g., in accordance with any of Method 1-1.19).

In another embodiment, the disclosure provides a method (Method 2) of making a topical gel formulation, e.g., any of Formulation 1-1.59, comprising
 i. providing the following premixes:
  a. Premix A comprising a dispersion of gelling agent in water,
  b. Premix B comprising a dispersion of benzoyl peroxide in polyhydric alcohol and water,
  c. Premix C comprising clindamycin phosphate in aqueous solution,
  d. Premix D comprising a dispersion of micronized adapalene in polyhydric alcohol and water,
 ii. mixing Premix A and Premix D,
 iii. admixing Premix B to the mixture of step ii,
 iv. admixing Premix C to the mixture of step iii,
 v. adjusting the pH of the mixture of step iv to pH 5-6 to form a gel. For example, the disclosure provides
2.1. Method 2 wherein the gelling agent is selected from hydroxypropylcellulose, hydroxyethylcellulose, carboxyvinyl polymers (optionally crosslinked with allyl ethers of polyalcohols, e.g., carbomers), carboxyvinyl copolymers, polyacrylates, acrylate copolymers, acrylamide/sodium acryloyldimethyltaurate copolymers, polyvinyl alcohols, polyethylene oxides, propylene glycol alginates, methylcellulose, hydroxypropylmethylcellulose, xanthan gum, carrageenan gum, and combinations thereof.
2.2. Any foregoing method wherein the gelling agent is selected from carboxyvinyl polymers (optionally cross-linked with allyl ethers of polyalcohols, e.g., carbomers), carboxyvinyl copolymers, polyacrylates, acrylate copolymers, acrylamide/sodium acryloyldimethyltaurate copolymers, propylene glycol alginates, hydroxypropylmethylcellulose, and xanthan gum.
2.3. Any foregoing method wherein the gelling agent comprises acrylamide/sodium acryloyldimethyltaurate copolymer.
2.4. Any foregoing method wherein the gelling agent comprises acrylamide sodium acryloyldimethyltaurate/ isohexadecane/polysorbate 80 gelling agent.
2.5. Any foregoing method wherein the gelling agent comprises a carbomer homopolymer, crosslinked with allyl ethers of polyalcohols (e.g., allyl sucrose or allyl pentaerythritol).
2.6. Any foregoing method wherein the gelling agent is a polymer of acrylic acid cross-linked with allyl ethers of polyalcohols; e.g., containing from 56% to 68% of carboxylic acid (—COOH) groups; e.g., having a viscosity of 40,000-60,000 cPs (measured at 0.5 wt % at pH 7.5).

2.7. Any foregoing method wherein the gelling agent is a carbomer homopolymer Type C, e.g., as defined by the United States Pharmacopeia/National Formulary (USP/NF) monograph, e.g., Carbopol 980.

2.8. Any foregoing method wherein the polyhydric alcohol is selected from propylene glycol, ethoxydiglycol, polyethylene glycol (e.g., PEG 400), glycerol, and combinations thereof.

2.9. Any foregoing method wherein the polyhydric alcohol is selected from 1,2-propylene glycol and 1,3-proylene glycol.

2.10. Any foregoing method wherein the polyhydric alcohol is 1,2-propylene glycol.

2.11. Any foregoing method wherein the amount of active ingredient in the final product is about 1.2 wt. % clindamycin phosphate, about 3.1 wt. % benzoyl peroxide, and about 0.15 wt. % adapalene.

2.12. Any foregoing method wherein the topical gel formulation thus produced comprises
about 1.2 wt. % clindamycin
phosphate, about 3.1 wt. % benzoyl
peroxide, about 0.15 wt. % adapalene,
about 5 wt. % propylene glycol,
about 1.75 wt. % carbomer homopolymer Type C,
potassium hydroxide in an amount to provide a pH of 5-6, and
water.

2.13. Any foregoing method wherein the pH of Premix C is adjusted to pH 6-7, e.g., pH 6.2-6.8.

2.14. Any foregoing method wherein in step v, the pH is adjusted to 5.4-5.8.

2.15. Any foregoing method wherein the pH adjusting agent is selected from sodium hydroxide, potassium hydroxide and mixtures thereof.

2.16. Any foregoing method wherein the pH adjusting agent is potassium hydroxide.

2.17. Any foregoing method further comprising the step of filling a dispensing container, e.g. a deformable tube or a pump container, with the product of step V.

The disclosure further provides a topical gel formulation, e.g., according to any of Formulations 1-1.59, which is the product of any of Methods 2-2.17.

Unless stated otherwise, all percentages of composition components given in this specification are by weight based on a total composition or formulation weight of 100%.

The compositions and formulations as provided herein are described and claimed with reference to their ingredients, as is usual in the art. As would be evident to one skilled in the art, the ingredients may in some instances react with one another, so that the true composition of the final formulation may not correspond exactly to the ingredients listed. Thus, it should be understood that the invention extends to the product of the combination of the listed ingredients.

"About" with respect to an amount or a concentration means 80% to 120%, 90% to 110% of the claimed value.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

The invention is further illustrated in the following examples, which are meant to be exemplary and not limiting.

EXAMPLES

Example 1: Clinical Trial Comparing Triple Combination with Double Combinations

This study is intended to evaluate the safety and efficacy of a novel, fixed-dose combination of clindamycin phosphate (CP), benzoyl peroxide (BPO), and adapalene (1.2%/3.1%/0.15%), relative to its vehicle and dual component combinations (BPO/Adapalene, clindamycin/BPO, and clindamycin/adapalene) for the treatment of moderate to severe acne vulgaris in subjects 9 years of age and older.

This is a multicenter, randomized, double-blind, vehicle-controlled, 12-week study designed to assess the safety, tolerability, and efficacy of combination of the triple combination gel containing clindamycin phosphate (CP), benzoyl peroxide (BPO), and adapalene (1.2%/3.1%/0.15%), relative to its vehicle and dual component combinations (BPO/Adapalene, clindamycin/BPO, and clindamycin/adapalene at weeks 2, 4, 8, and 12. The formulations tested are as follows:

TABLE 1

| Ingredient | Test Gel % w/w | A: Adap/BPO % w/w | B: CP/BPO % w/w | C: CP/Adap % w/w | Vehicle % w/w |
|---|---|---|---|---|---|
| Clindamycin phosphate | 1.2 | | 1.2 | 1.2 | |
| a. Benzoyl peroxide, hydrous (weight on anhydrous basis) | 3.1 | 3.1 | 3.1 | | |
| Adapalene | 0.15 | 0.15 | | 0.15 | |
| Propylene glycol | 5.0 | 5.0 | 5.0 | 5.0 | 5.0 |
| Carbopol 980 (Carbomer homopolymer) | 1.75 | 1.75 | 1.75 | 1.75 | 1.75 |
| TiO2 | | | | | 0.25 |
| Methylparaben | | | | 0.17 | 0.17 |
| Propylparaben | | | | | 0.03 |
| Potassium hydroxide | Qs pH 5.0-6.0 | Qs pH 5.0-6.0 | Qs pH 5.0-6.0 | Qs pH 5.0-6.0 | Qs pH 5.0-6.5 |
| Purified Water | qs to 100% | qs to 100% | qs to 100% | qs to 100% | qs to 100% |

To be eligible for the study, subjects must be at least 9 years of age and have a clinical diagnosis of moderate to severe acne (defined as an Evaluator's Global Severity Score [EGSS, described above] of 3 or 4), presenting with 30-100 inflammatory facial lesions (papules, pustules, and nodules), 35-150 non-inflammatory facial lesions (open and closed comedones), and ≤2 facial nodules. All subjects receive once daily, topically applied treatment to the face for 12 weeks. Subject visits include Screening, Baseline, Week 2, Week 4, Week 8, and Week 12, at which safety and efficacy assessments are conducted (Screening and Baseline may occur on the same day if no washout is required). One pump of study drug is dispensed to the subjects at the Baseline, Week 4, and Week 8 study visits. Subjects are evaluated for drug usage compliance at each post baseline study visit (Weeks 2, 4, 8, and 12). Subjects apply their treatments at home, once daily (in the evening), as instructed by the study coordinator or designee at each study center.

The investigator assesses the subject's face at each study visit. Information on reported and observed adverse events (AEs) is obtained at each visit. An abbreviated physical examination and vital sign measurements is performed at Baseline and Week 12 (end of study) for all subjects. Blood samples are collected from subjects at Baseline and Week 12, for CBC/Diff and serum chemistry. For all female subjects of childbearing potential (FOCBP), urine pregnancy testing is performed at Screening, Baseline (prior to randomization), and at Weeks 2, 4, 8, and 12. Additionally, serum pregnancy testing is performed at Baseline and Week 12. In addition, at selected study centers, standardized photography of the face is performed at Baseline, and Weeks 4, 8 and 12.

Approximately 750 subjects are randomized in a 1:1:1:1:1 ratio to the following treatment groups:
150 Subjects to Test Gel (clindamycin phosphate 1.2%/BPO 3.1%/adapalene 0.15%)
150 Subjects to Component A (BPO 3.1%/adapalene 0.15%)
150 Subjects to Component B (clindamycin phosphate 1.2%/BPO 3.1%)
150 Subjects to Component C (clindamycin phosphate 1.2%/adapalene 0.15%)
150 Subjects to Vehicle Gel The assigned study drug is applied topically to the face once daily at home, in the evening, for 12 weeks (up to the evening prior to the Week 12 visit), with the exception of study visit days (Baseline, Week 2, 4 and 8) where study drug is applied (also by the subject) after the study visit is completed, at the investigational center.

Subjects meeting all of the following criteria are eligible for study entry:
1. Male or female at least 9 years of age and older.
2. Written and verbal informed consent must be obtained. Subjects less than age of consent must sign an assent for the study and a parent or a legal guardian must sign the informed consent (if subject reaches age of consent during the study they should be re-consented at the next study visit).
3. Subject must have an EGSS of 3 (moderate) or 4 (severe) at the baseline visit.
4. Subjects with a facial acne inflammatory lesion (papules, pustules, and nodules) count no less than 30, but no more than 100.
5. Subjects with a facial acne non-inflammatory lesion (open and closed comedones) count no less than 35, but no more than 150.
6. Subjects with 2 or fewer facial nodules.
7. FOCBP1 and females who are premenses must be willing to practice effective contraception for the duration of the study. (Effective contraception is defined as stabilized on oral contraceptive for at least 3 months, intrauterine device, condom with spermicide, diaphragm with spermicide, implant, NuvaRing®, injection, transdermal patch or abstinence.) Females on birth control pills must have taken the same type pill for at least 3 months prior to entering the study and must not change type during the study. Those who have used birth control pills in the past must have discontinued usage at least 3 months prior to the start of the study. Women who use birth control for acne control only should be excluded.
8. Premenses females and FOCBP must have a negative urine pregnancy test at the Screening Visit, and a negative urine pregnancy test at the Baseline Visit.
9. Subjects must be willing to comply with study instructions and return to the clinic for required visits. Subjects under the age of consent must be accompanied by the parent or legal guardian at the time of assent/consent signing.
10. If a cleanser, moisturizer or sunscreen is needed during the study, subjects must be willing to use only allowed cleansers, moisturizers, sunscreens, or moisturizer/sunscreen combination products (see Appendix 17.2). The subject must agree to use non-comedogenic products (including makeup and shaving products).

Subjects meeting any of the following criteria are excluded from the study:
1. Use of an investigational drug or device within 30 days of enrollment or participation in a research study concurrent with this study.
2. Any dermatological conditions on the face that could interfere with clinical evaluations such as acne conglobata, acne fulminans, secondary acne, perioral dermatitis, clinically significant rosacea, Gram-negative folliculitis, dermatitis, eczema.
3. Any underlying disease(s) or some other dermatological condition of the face that requires the use of interfering topical or systemic therapy or makes evaluations and lesion count inconclusive.
4. Subjects with a facial beard or mustache that could interfere with the study assessments.
5. Subjects with more than two (2) facial nodules.
6. Evidence or history of cosmetic-related acne.
7. Subject has a history of experiencing significant burning or stinging when applying any facial treatment (eg, makeup, soap, masks, washes, sunscreens, etc) to their face.
8. Female subjects who are pregnant, nursing mothers, planning a pregnancy during the course of the study, or become pregnant during the study.
9. Use of estrogens (eg, Depogen, Depo-Testadiol, Gynogen, Valergen, etc) for less than 12 weeks immediately preceding study entry; subjects treated with estrogens 12 or more consecutive weeks immediately prior to study entry need not be excluded unless the subject expects to change dose, drug or discontinue estrogen use during the study.
10. If female, subject has a history of hirsutism, polycystic ovarian disease or clinically significant menstrual irregularities.
11. History of regional enteritis, ulcerative colitis, inflammatory bowel disease, pseudomembranous colitis, chronic or recurrent diarrhea, or antibiotic-associated colitis.

12. Treatment of any type of cancer within the last 6 months, with the exception of complete surgical excision of skin cancer outside the treatment area.
13. Subject uses medications and/or vitamins during the study which are reported to exacerbate acne (azathioprine, haloperidol, Vitamin D, Vitamin B12, halogens such as iodides or bromides, lithium, systemic or topical mid to super-high potency corticosteroids on the treatment area, phenytoin and phenobarbital). Multivitamins, including Vitamin A, at recommended daily doses, and Vitamin D at stable doses, are acceptable.
14. History of hypersensitivity or allergic reactions to any of the study preparations as described in the Investigator's Brochure, including known sensitivities to any dosage form of clindamycin phosphate, BPO, or adapalene.
15. Concomitant use of potentially irritating over-the-counter products that contain ingredients such as BPO, alpha-hydroxy acid, salicylic acid, retinol or glycolic acids.
16. Subjects who have not undergone the specified washout period(s) for the following topical preparations or physical treatments used on the face or subjects who require the concurrent use of any of the following in the treatment area:
    Topical astringents and abrasives (including comedone removal strips) on the face: 1 week
    Non-allowed moisturizers or sunscreens on the face: 1 week
    Antibiotics on the face: 2 weeks
    Other topical anti-acne drugs on the face: 2 weeks
    Soaps containing antimicrobials on the face: 2 weeks
    Anti-inflammatory agents and corticosteroids on the face: 4 weeks
    Retinoids, including retinol on the face: 4 weeks
    Facial procedures, including chemical peel, microdermabrasion, light (PDT, LED) and laser therapy, and acne surgery: 4 weeks
    If the subject requires topical treatment for acne on areas other than the face (e.g., chest and/or back), the investigator may prescribe a product that does not contain clindamycin phosphate, BPO, or adapalene, and must be noted in the source documents and the electronic case report form (eCRF).
17. Subjects who have not undergone the specified washout period(s) for the following systemic medications or subjects who require the concurrent use of any of the following systemic medications:
    Corticosteroids (including intramuscular injections) (inhaled corticosteroids are allowed): 4 weeks
    Antibiotics: 4 weeks
    Other systemic acne treatments: 4 weeks
    Systemic retinoids: 6 months
18. Subject intends to use a tanning booth or sunbathe during the study.
19. Subjects who are unable to communicate or cooperate with the investigator due to language problems, poor mental development, or impaired cerebral function.
20. Subjects with any underlying disease that the investigator deems uncontrolled, and poses a concern for the subject's safety while participating in the study.

Subject Withdrawal Criteria: Reasons for withdrawal may include, but are not limited to, the following:
Acne flare, as determined by the investigator, which requires treatment with a disallowed therapy.
Either at the investigator's request, for tolerability reasons (e.g., severe adverse reactions), or at the subject's request.
When the requirements of the protocol are not followed.
When a concomitant therapy likely to interfere with the results of the study is reported or required by the subject (the investigators report all such information on the source documents/eCRFs and decide, in accordance with the Sponsor, whether the subject is to be withdrawn).
When a subject is lost to follow-up. The investigators try twice to reach the subject by telephone, email and/or text message, and send a follow-up letter by certified mail before considering that the subject is lost to follow-up. These actions are reported on the End of Study source documents and the final eCRF, and a copy of the follow-up letter is maintained in the investigator's file.

All premature discontinuations and their associated reasons must be carefully documented by the investigator on source documents and the final eCRF, and, if need be, on the AE form. In any case, no subject who has been included and has an assigned study number can be replaced by another if the subject discontinues prematurely for whatever reason. All data gathered on the subject prior to termination is made available to the Sponsor.

Reasons for study completion/discontinuation as listed on the final report form are defined as follows:
Normal Study Completion—Subject completes the study as planned in the protocol.
Adverse Event—Complete an AE form.
Death—Complete a serious adverse event (SAE) form.
Subject Request—Consent withdrawal, subject moved, schedule conflicts.
Protocol Violation—Contact the Sponsor or designee before making decision.
Lost to Follow-Up—Document with 2 phone calls, emails and/or text messages, and a certified letter.
Pregnancy—Subject will discontinue study drug immediately, but will be followed to term.
Complete a pregnancy form.
Worsening Condition—Subject requires alternate treatment for acne before the end of the study and the investigator determines it is not due to lack of efficacy
Lack of Efficacy—Subject requires alternate treatment for acne after at least 2 weeks of study drug treatment and the risk of continuing the subject in the study outweighs the benefit as determined by the investigator.
Withdrawal by Parent/Guardian—An indication that the study participant has been removed from the study by the parent or legal guardian; includes consent withdrawal, subject moves, schedule conflicts, etc.
Study Terminated by Sponsor—An indication that a clinical study was stopped by its Sponsor.
Other—Specify in the comments section of the eCRF.

Criteria for Evaluation:
Primary Efficacy:
The co-primary efficacy endpoints are intended to compare the numerical superiority of once daily application of Test Gel with Vehicle Gel and each of the gel comparators (Components A, B and C). Specifically, the endpoints to be summarized using descriptive and inferential statistics are:
(1) Absolute change from Baseline to Week 12 in mean inflammatory lesion counts.
(2) Absolute change from Baseline to Week 12 in mean non-inflammatory lesion counts.

(3) Percent of subjects who achieve at least a 2-grade reduction from baseline and are "clear" or "almost clear" at Week 12 based on the Evaluator's Global Severity Score (EGSS).

Secondary Efficacy:

The secondary efficacy endpoints are intended to compare the numerical superiority of once daily application of Test Gel with Vehicle Gel and each of the gel comparators (Components A, B and C). Specifically, the secondary endpoints to be summarized using descriptive statistics are:
(1) Absolute change in inflammatory and non-inflammatory lesion counts from baseline at Weeks 2, 4, and 8.
(2) Percent of subjects who achieve at least a 2-grade reduction from baseline and are "clear" or "almost clear" at Week 2, 4, and 8 based on the EGSS.
(3) Mean percent change in inflammatory and non-inflammatory lesion counts from baseline at Weeks 2, 4, 8, and 12.

Efficacy Measurements:

Lesion Counts: At each visit, the evaluator counts the total number of inflammatory lesions (papules, pustules, and nodules) on the subject's face. Nodules are counted separately, but are included in the total inflammatory lesion count. At baseline, eligible subjects may have no more than 2 nodules. Nodules are included in the statistical analysis of inflammatory lesion counts. All inflammatory lesions are counted at the same time rather than counting papules and pustules separately. The evaluator also counts the total number of non-inflammatory lesions (open and closed comedones). The same blinded evaluator performs the lesion counts and EGSS evaluations at all visits from baseline to week 12 for the same subject.

Inflammatory lesions are defined as follows:
Papule—a small, solid elevation less than 5 mm in diameter. Most of the lesion is above the surface of the skin.
Pustule—a small, circumscribed elevation less than 5 mm in diameter that contains yellow-white exudate.
Nodule—a subcutaneous lesion greater than or equal to 5 mm in diameter.

Non-inflammatory lesions are defined as follows:
Open comedones (black head)—a lesion in which the follicle opening is widely dilated with the contents protruding out onto the surface of the skin.
Closed comedones (white head)—a lesion in which the follicle opening is closed, but the sebaceous gland is enlarged by the pressure of the sebum build up, which in turn causes the skin around the follicle to thin and become elevated with a white appearance.

Evaluator's Global Severity Score (EGSS): At each visit, the severity is determined based on evaluator-blinded evaluations of the signs and symptoms of acne vulgaris. Every effort should be made to have the same evaluator assess the same subject at each visit. If this is not possible, the same evaluator should assess the subject at both the Baseline and Week 12 visits. Evaluations are scored on a scale of 0-4, with 0 being clear and 4 being severe:

TABLE 2

| Score | Grade | Description |
|---|---|---|
| 0 | Clear | Normal, clear skin with no evidence of acne vulgaris |
| 1 | Almost clear | Rare non-inflammatory lesions present, with rare non-inflamed papules (papules must be resolving and may be hyperpigmented, though not pink-red) |
| 2 | Mild | Some non-inflammatory lesions are present, with few inflammatory lesions (papules/pustules only; no nodulocystic lesions) |
| 3 | Moderate | Non-inflammatory lesions predominate, with multiple inflammatory lesions evident: several to many comedones and papules/pustules, and there may or may not be one nodulocystic lesion |
| 4 | Severe | Inflammatory lesions are more apparent, many comedones and papules/pustules, there may or may not be up to two nodulocystic lesions |

The EGSS should always be completed prior to the lesion counts.

Safety Measurements: Safety evaluations include the following:
The percent of subjects who experience a cutaneous reaction (erythema, scaling, hypo/hyper-pigmentation, itching, burning, or stinging) graded at a level of 3 at any point in the study following the first application of study drug.
The percent of subjects who experience a cutaneous adverse event (AE) irrespective of severity grade at any point in the study following the first application of study drug.
Changes from baseline in all safety laboratory values and vital sign measurements as summarized using descriptive statistics by treatment group and study visit.
Subjects are assessed for the occurrence of new and ongoing AEs.

Cutaneous safety and tolerability are evaluated by tabulations of AEs and Cutaneous Safety and Tolerability Evaluation scores (scaling, erythema, hypo/hyper-pigmentation, itching, burning, and stinging) to be assessed at each study visit. Itching, burning and stinging (cutaneous tolerability) are reviewed with the subject at each study visit as an average over the period since the previous visit. Scaling, erythema, and hypo/hyper-pigmentation (cutaneous safety) are assessed by the evaluator at each visit. Cutaneous tolerability signs and symptoms that result in the subject requiring a concomitant therapy, interruption of treatment, or discontinuation from the study are reported as an AE.

Statistical Methods: All statistical processing are performed using SAS® version 9.3 or later unless otherwise stated.

Statistical significance is based on two-tailed tests of the null hypothesis resulting in p-values of 0.05 or less. P-values for selected variables are presented to assist the reviewer in evaluating the outcome of the study. Failure to achieve a statistically significant result at an alpha level of 0.05 does not imply a failed study.

The absolute change in mean inflammatory and non-inflammatory lesion counts from baseline to Week 12 is analyzed with an analysis of covariance (ANCOVA) with factors of treatment group and analysis center and a covariate of their respective baseline lesion count. A non-parametric analysis may be used. Additionally, 4 pairwise tests are conducted comparing the Test Gel to Vehicle Gel and Test Gel to each of the dual component gels.

The percent of subjects with treatment success, defined as at least a 2-grade improvement from baseline in the EGSS and an EGSS equating to "clear" or "almost clear", are analyzed with a logistic regression test with factors of treatment group and analysis center and a covariate of baseline severity at Week 12. Four pairwise tests are conducted comparing the Test Gel to Vehicle Gel and Test Gel to each of the dual component gels.

The primary method of handling missing efficacy data is MCMC multiple imputation. Other methods, as well as the MCMC imputation, are specified in the statistical analysis plan which is finalized prior to data base lock.

Populations Analyzed and Treatment Groups: Inflammatory and non-inflammatory lesion counts are recorded for each subject at baseline and at Weeks 2, 4, 8, and 12. The absolute and percent change from baseline in inflammatory and noninflammatory lesions are derived for each subject at Weeks 2, 4, 8, and 12. The EGSS is recorded for each subject. The EGSS is dichotomized into "success" and "failure" with a subject considered a success if the EGSS at Weeks 2, 4, 8, and 12 is at least 2 grades less than baseline and achieving "clear" or "almost clear." An intent-to-treat (ITT) analysis is conducted on all study subjects. The ITT population consists of all randomized subjects who received study drug. The safety population consists of all randomized subjects who are presumed to have used the study drug at least once and who provide at least 1 post-baseline evaluation. A per-protocol (PP) analysis is also conducted.
Subjects are eligible for the PP analysis if they complete the 12-week evaluation without noteworthy study protocol violations (i.e., any subject or investigator activity that could have possibly interfered with the therapeutic administration of the treatment or the precise evaluation of treatment efficacy). The PP population includes subjects in the ITT population who do not meet any of the following criteria:
Failed any of the inclusion/exclusion criteria.
Have taken any interfering concomitant medications.
Did not attend the Week 12 visit, with the exception of a discontinuation from the study due to an AE related to study treatment or documented lack of treatment effect.
Missed more than 1 post baseline study visit prior to Week 12
Have not been compliant with the dosing regimen (i.e., subjects may not miss more than 5 consecutive days of dosing and must take 80%-120% of expected doses). The number of expected doses is determined for each subject based on the length of their participation in the study.
Out of visit window at the Week 12 visit.
Prior to breaking the blind, other additional criteria may be added to the list to accommodate for unforeseen events that occurred during the conduct of the trial that result in noteworthy study protocol violations.

Subject demographic and baseline characteristics are summarized by treatment group using descriptive statistics for the ITT, PP, and safety analysis sets.

Efficacy Evaluation—Primary: Co-primary efficacy analyses of the absolute change in inflammatory and in non-inflammatory lesions, from baseline, is conducted on the ITT population. The pre-specified time point is Week 12. Descriptive statistics are presented by treatment group for inflammatory and for non-inflammatory lesions as well as the absolute change in inflammatory and in non-inflammatory lesions. All of the testing relating to the analysis of inflammatory and non-inflammatory lesions uses the methods described above. The co-primary analysis of the dichotomized EGSS (success being at least a 2-grade improvement and achieving "clear" or "almost clear") for the ITT population is based on the logistic regression test with factors of treatment group and analysis center and a covariate of baseline severity.

Efficacy Evaluation—Secondary: Mean percent change in inflammatory and non-inflammatory lesion counts from baseline, as well as proportion of subjects with at least a 2-grade improvement in the EGSS from baseline, is evaluated at Weeks 2, 4, 8, and 12.

Safety Evaluation: All subjects who receive medication and provide at least 1 post-baseline evaluation constitute the safety population. Safety is evaluated by tabulations of AEs, Cutaneous Safety and Tolerability Evaluations, vital signs/abbreviated physical examinations, and safety laboratory results. Cutaneous Safety and Tolerability Evaluation scores (erythema, scaling, hypo/hyper-pigmentation, itching, burning, and stinging) are presented with descriptive statistics at baseline and at Weeks 2, 4, 8, and 12 for each treatment group. Frequencies and percentages for each outcome category are included in these statistics. Mean values are presented graphically by week and treatment group. Vital sign measurements, an abbreviated physical examination, and safety laboratory results are conducted on all subjects at specified visits. For pre-menses females and FOCBP, urine pregnancy and serum pregnancy testing occur at specified visits. Changes from baseline in safety laboratory values and vital sign measurements are summarized with descriptive statistics for each treatment group at all applicable study visits. Shift tables are presented for changes in safety laboratory values to summarize laboratory test results collected at Baseline and Week 12. Normal ranges established by the central laboratory are used to determine the shifts. A listing of all out-of-range laboratory test results at any assessment time point is also be provided. Determination of clinical significance for all out-of-range laboratory values is made by each investigator and included in the listing. In addition, a listing of all clinically significant laboratory test results is provided.

All previous concomitant medications are classified based on terminology from the World Health Organization Drug Dictionary. Previous therapies and concomitant medications data are presented in the data listings. All AEs occurring during the study are recorded and classified using the Medical Dictionary for Regulatory Activities (MedDRA) terminology. Descriptions of AEs include the date of onset, the date the AE ended, the severity of the AE, the relationship to study drug, the action taken regarding study drug usage, the action taken to treat the AE, and the outcome. Adverse events are summarized by treatment group and severity. Each subject is counted only once within a system organ class or a preferred term
by using the AEs with the highest severity within each category. Adverse events are summarized by treatment group and relationship to study drug. Each subject is counted only once within a system organ class or a preferred term by using the AEs with the greatest relationship within each category. All information pertaining to AEs noted during the study is listed by subject, detailing the verbatim descriptions given by the investigator, preferred term, system organ class, start date, stop date, severity, actions taken, and drug relatedness. The AE onset is also be shown relative (in number of days) to the day of initial dose of the randomized study drug. Serious adverse events (SAEs) is tabulated by subject within treatment groups. In addition, a list of subjects who discontinued from the study and a list of subjects who experienced SAEs is also provided.

Subject Self-Assessments: Subjects are asked to complete an Acne-Specific Quality of Life Questionnaire during the study. The Investigator assessments (EGSS and lesion counts) are conducted independently of this subject self-assessment. Inferential statistical analysis is not performed on the questionnaire; the subjective responses are compared between treatment groups for trends.

This study is performed in compliance with Good Clinical Practice including the archiving of essential study documents. This protocol follows guidelines outlined by the International Conference for Harmonisation.

The clinical trial shows that the Test Gel is significantly more effective than vehicle or any of the three two-component comparators:

TABLE 3

Primary Efficacy Analysis: Absolute Change from Baseline in Lesion Counts and Dichotomized Global Severity at Week 12 (Intent-to-Treat Population)

|  | Test Gel (N = 146) CP/BPO/Adap | A gel (N = 150) BPO/Adap | B gel (N = 146) CP/BPO | C gel (N = 150) CP/Adap | Vehicle gel (N = 148) | Skewness P-Value | Overall P-Value |
|---|---|---|---|---|---|---|---|
| Inflammatory Lesion Count - Absolute Change from Baseline | | | | | | | |
| LSMean$^a$ | −29.9 | −26.7 | −24.8 | −26.8 | −19.6 | <0.001$^c$ | <0.001$^a$ |
| LSSD$^a$ | 11.86 | 11.74 | 11.71 | 11.69 | 12.12 | | <0.001$^d$ |
| Median$^b$ | −29.5 | −27.2 | −27.0 | −26.8 | −19.8 | | |
| Min. to Max.$^b$ | −79 to 10 | −67 to 6 | −83 to 93 | −74 to 2 | −51 to 14 | | |
| P-Value vs. Test Gel$^a$ | | 0.021 | <0.001 | 0.027 | <0.001 | | |
| P-Value vs. Test Gel$^d$ | | 0.013 | 0.003 | 0.026 | <0.001 | | |
| Non-Inflammatory Lesion Count - Absolute Change from Baseline | | | | | | | |
| LSMean$^a$ | −35.5 | −29.9 | −27.8 | −30.0 | −21.8 | <0.001$^c$ | <0.001$^a$ |
| LSSD$^a$ | 16.25 | 16.40 | 15.97 | 16.40 | 16.58 | | <0.001$^d$ |
| Median$^b$ | −33.6 | −30.1 | −29.8 | −31.4 | −23.5 | | |
| Min. to Max.$^b$ | −94 to 5 | −93 to 26 | −65 to 30 | −99 to 36 | −76 to 39 | | |
| P-Value vs. Test Gel$^a$ | | 0.003 | <0.001 | 0.004 | <0.001 | | |
| P-Value vs. Test Gel$^d$ | | 0.004 | <0.001 | 0.005 | <0.001 | | |
| Evaluator Global Severity Score - At Least Two Grade Reduction from Baseline and Clear or Almost Clear | | | | | | | |
| Success | 52.5% | 27.8% | 30.5% | 30.3% | 8.1% | N/A | <0.001$^e$ |
| Failure | 47.5% | 72.2% | 69.7% | 69.7% | 91.9% | | |
| P-Value vs. Test Gel$^e$ | | <0.001 | 0.001 | 0.001 | <0.001 | | |

$^a$Least squares means, standard deviations, contrast p-values and overall p-value from an analysis of covariance with factors of treatment group and analysis center and the respective baseline lesion count as a covariate. Values adjusted for multiple imputation.

$^b$Median, minimum and maximum represent average values, obtained from averaging the summary statistics generated from each imputed dataset.

$^c$Skewness test, assessed for each imputed dataset. The average p-value is presented.

$^d$Contrast p-values and overall p-value from a ranked analysis of covariance with factors of treatment group and analysis center and the respective baseline lesion count as a covariate. Values adjusted for multiple imputation.

$^e$Contrast p-values and overall p-value from a logistic regression with factors of treatment group and analysis center. Values adjusted for multiple imputation.

Note:

Multiple imputation (MCMC) used to impute missing values. Change calculated as Week 12 - baseline.

Not only was the three-component Test Gel more effective than the two-component comparators, but it had fewer side effects than the benzoyl peroxide/adapalene combination:

TABLE 4

Summary of Treatment-Emergent Adverse Event Characteristics (Safety Population)

| | Test Gel (N = 141) CP/BPO/Adap | A gel (N = 146) BPO/Adap | B gel (N = 144) CP/BPO | C gel (N = 148) CP/Adap | Vehicle gel (N = 146) |
|---|---|---|---|---|---|
| Subjects reporting any adverse event | 51 (36.2%) | 52 (35.6%) | 26 (18.1%) | 40 (27.0%) | 22 (15.1%) |
| Subjects reporting any serious adverse event | 1 (0.7%) | 0 (0.0%) | −0 (0.0%) | −26.8 | 0 (0.0%) |
| Subjects who died | 0 (0.0%) | 0 (0.0%) | 0 (0.0%) | 0 (0.0%) | 0 (0.0%) |
| Subjects who prematurely discontinued study drug due to an adverse event | 4 (2.8%) | 8 (5.5%) | 0 (0.0%) | 3 (2.0%) | 2 (1.4%) |
| Subjects who prematurely discontinued from the study due to an adverse event | 4 (2.8%) | 8 (5.5%) | 0 (0.0%) | 3 (2.0%) | 1 (0.7%) |
| Total number of adverse events reported By Subject | 90 | 96 | 35 | 74 | 30 |
| Maximum severity | | | | | |
| Severe | 7 (5%) | 5 (3.4%) | 0 (0.0%) | 3 (2.0%) | 1 (0.7%) |
| Moderate | 18 (12.8%) | 22 (15.1%) | 10 (6.9%) | 17 (11.5%) | 10 (6.8%) |
| Mild | 26 (18.4%) | 25 (17.1%) | 16 (11.1%) | 20 (13.5%) | 11 (17.5%) |
| Strongest relationship to study drug | | | | | |
| Related | 28 (19.9%) | 32 (21.9%) | 3 (2.1%) | 18 (12.2%) | 2 (1.4%) |
| Not related | 23 (16.3%) | 20 (13.7%) | 23 (16.0%) | 22 (14.9%) | 20 (13.7%) |
| Maximum severity within relationship to study drug | | | | | |
| Related | | | | | |
| Severe | 5 (3.5%) | 5 (3.4%) | 0 (0.0%) | 1 (0.7%) | 0 (0.0%) |
| Moderate | 10 (7.1%) | 13 (8.9%) | 0 (0.0%) | 8 (5.4%) | 1 (0.7%) |
| Mild | 13 (9.2%) | 14 (9.6%) | 3 (2.1%) | 9 (6.1%) | 1 (0.7%) |
| Not related | | | | | |
| Severe | 2 (1.4%) | 0 (0.0%) | 0 (0.0%) | 2 (1.4%) | 1 (0.7%) |
| Moderate | 9 (6.4%) | 11 (7.5%) | 10 (6.9%) | 11 (7.4%) | 9 (6.2%) |
| Mild | 18 (12.8%) | 16 (11.0%) | 16 (1.1%) | 11 (7.4%) | 11 (7.5%) |

Note:
Treatment-emergent adverse events are those with an onset on or after the date of the first dose of study drug.

The invention claimed is:

1. A topical gel formulation comprising:
   1-1.5 wt. % clindamycin phosphate;
   2.5-3.5 wt. % benzoyl peroxide comprising a plurality of benzoyl peroxide particles;
   0.15-0.2 wt. % adapalene comprising a plurality of adapalene particles;
   a gelling agent;
   an additional agent as a polyhydric alcohol; and
   water.

2. The topical gel formulation of claim 1, wherein the concentration of clindamycin phosphate is about 1.2 wt. %, the concentration of benzoyl peroxide is about 3.1 wt. %, and the concentration of adapalene is 0.15 wt. %.

3. The topical gel formulation of claim 2, wherein
   the polyhydric alcohol is propylene glycol in a concentration of about 5 wt. %,
   the gelling agent is carbomer homopolymer Type C in a concentration of about 1.75 wt. %,
   the formulation further comprising potassium hydroxide in an amount to provide a pH of 5-6.

4. The topical gel formulation of claim 1, wherein the formulation is stable at room temperature for at least six weeks.

5. The topical gel formulation of claim 1, wherein the formulation is stable at room temperature for at least ten weeks.

6. The topical gel formulation of claim 1, wherein the formulation is stable at 36° F. to 46° F., then stable at or below 77° F. for at least six weeks.

7. The topical gel formulation of claim 1, wherein the formulation is stable at 36° F. to 46° F. prior to dispensing to a patient, then stable at or below 77° F. for at least 10 weeks.

8. The topical gel formulation of claim 1, wherein the gelling agent is selected from the group consisting of hydroxypropylcellulose, hydroxyethylcellulose, carboxyvinyl polymers, carboxyvinyl polymers crosslinked with allyl ethers of polyalcohols, carboxyvinyl copolymers, polyacrylates, acrylate copolymers, acrylamide/sodium acryloyldimethyltaurate copolymers, polyvinyl alcohols, polyethylene oxides, propylene glycol alginates, methylcellulose, hydroxypropylmethylcellulose, xanthan gum, carrageenan gum, and combinations thereof.

9. The topical gel formulation of claim 1, wherein the gelling agent comprises carbomer homopolymer Type C.

10. The topical gel formulation of claim 1, wherein the gelling agent is a crosslinked polymer comprising carboxy moieties and wherein the formulation further comprises a base selected from the group consisting of potassium hydroxide, sodium hydroxide and combinations thereof in an amount sufficient to deprotonate the carboxy moieties sufficiently to cause the gelling agent to thicken.

11. The topical gel formulation of claim 1, wherein the amount of gelling agent is 1.5 wt. % to 2 wt. %.

12. The topical gel formulation of claim 1, wherein the plurality of benzoyl peroxide particles is homogeneously dispersed in the formulation.

13. The topical gel formulation of claim 1, wherein the plurality of benzoyl peroxide particles has a mean particle size between 1 and 50 microns.

14. The topical gel formulation of claim 11, wherein the plurality of adapalene particles is homogeneously dispersed in the formulation.

15. The topical gel formulation of claim 1, wherein the adapalene and the benzoyl peroxide do not undergo any detrimental interaction with one another.

16. The topical gel formulation of claim 1, wherein the polyhydric alcohol is selected from the group consisting of propylene glycol, ethoxydiglycol, polyethylene glycol, and glycerol.

17. The topical gel formulation of claim 1, wherein the formulation is free of additional agents as organic solvents other than the polyhydric alcohol.

18. The topical gel formulation of claim 1, wherein the amount of polyhydric alcohol is 3 wt. % to 7 wt. %.

19. The topical gel formulation of claim 1, wherein the formulation is free of ionic surfactants.

20. The topical gel formulation of claim 1, wherein the formulation is free of preservatives other than the polyhydric alcohol.

* * * * *